United States Patent [19]

Henrick et al.

[11] 4,032,564

[45] June 28, 1977

[54] ESTERS OF CYCLOPROPYLALKANOLS

[75] Inventors: Clive A. Henrick; Gerardus B. Staal, both of Palo Alto, Calif.

[73] Assignee: Zoecon Corporation, Palo Alto, Calif.

[22] Filed: Jan. 29, 1976

[21] Appl. No.: 653,401

Related U.S. Application Data

[63] Continuation-in-part of Ser. No. 504,223, Sept. 9, 1974, abandoned.

[52] U.S. Cl. .................. 260/481 R; 260/484 R; 260/526 S; 260/535 R; 424/311; 424/314
[51] Int. Cl.$^2$ ............... C07C 69/67; C07C 69/73; C07C 149/20
[58] Field of Search ................ 260/481 R, 484 R

[56] References Cited

UNITED STATES PATENTS

| 2,416,052 | 2/1947 | Gribbins | 260/481 R |
| 2,535,875 | 12/1950 | Stewart | 260/481 R |
| 2,936,856 | 5/1960 | Braunwarth et al. | 260/484 R |
| 3,061,619 | 10/1962 | Braunwarth et al. | 260/481 R |

FOREIGN PATENTS OR APPLICATIONS

| 1,393,677 | 2/1965 | France | 260/481 R |

OTHER PUBLICATIONS

Fieser et al., Org. Chemistry, 3rd ed., 1958, pp. 46–47.

Primary Examiner—Vivian Garner
Attorney, Agent, or Firm—Donald W. Erickson

[57] ABSTRACT

Esters of cyclopropyl substituted alcohols, syntheses thereof, compositions thereof, and use for the control of mites and ticks.

8 Claims, No Drawings

ESTERS OF CYCLOPROPYLALKANOLS

This is a continuation-in-part of Ser. No. 504,223, filed September 9, 1974, now abandoned.

This invention relates to novel compounds, syntheses thereof, compositions thereof and the control of mites.

The compounds of the present invention are effective for the control of mites and especially spider mites. Spider mites are plant feeders and cause serious damage to orchard trees, field crops, greenhouse plants and other vegetation. They feed on the foliage and fruit of plants and trees and, due to their wide distribution and polyphagous feeding habits, attack a variety of plants and trees. Spider mites of the family Tetranychidae, such as *Tetranychus urticae, Tetranychus canadensis, Tetranychus cinnabarinus, Tetranychus pacificus, Bryobia praetiosa, Oligonychus pratensis, Oligonychus ilicis, Panonychus citri, Panonychus ulmi*, and similar related species, are of particular biological interest and economic importance. Other mites are those of the family Tarsonemidae, such as *Steneotarsonemus pallidus*.

Compounds of the present invention of the following formula I are effective control agents for mites.

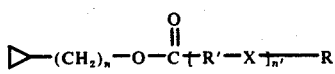     (I)

wherein,
R is alkyl of one to eighteen carbon atoms, alkenyl of two to eighteen carbon atoms or alkynyl of two to eighteen carbon atoms;
R' is methylene or ethylene;
X is oxygen or sulfur;
n is an odd integer between one and thirteen; and
n' is one, two or three;
with the proviso that each compound contains at least twelve carbon atoms in the molecule.

Hereinafter, each of R, R', X, n and n' is as defined above unless otherwise specified.

The compounds of formula I are applied to the mite particularly during the egg, larval or nymphal stages in view of their effect in causing egg mortality, abnormal development leading to death, inability to pass from one stage to the next, inability to reproduce and death. Some of the compounds also exhibit a residual ovicidal effect on foliage. A compound of formula I can be applied at concentration levels of the order of 0.001% to 1%, usually 0.01% to 0.1% by weight. Suitable carrier substances include liquid or solid inert carriers, such as water, acetone, xylene, mineral or vegetable oils, talc, vermiculite and silica. Treatment of mites in accordance with the present invention can be accomplished by spraying, dusting, or otherwise contacting the mites and/or their eggs or larvae directly or indirectly. Generally, a concentration of less than 25% of active compound in the formulation is used depending on the type of application apparatus. The formulations can include emulsifying agents and wetting agents to assist in the application and effectiveness of the active ingredient.

The esters of formula I can be prepared by reacting a cyclopropyl substituted alcohol

with one mole of an acid of the formula

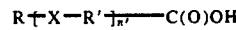

in the presence of an acid catalyst and with heating. The reaction can be carried out in the absence of a solvent; however, use of a solvent inert to the reaction, such as an ether or hydrocarbon solvent, is preferred. Water may be removed by distillation, if desired.

Alternatively, the appropriate acid halide

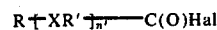

may be reacted with the alcohol

in the presence of pyridine and at either room temperature or, when the alcohol is sensitive to mineral acid, at from about −10 to about 0° C.

The preparation of the alcohols

where n 1 is described in copending application Ser. No. 489,279, filed July 17, 1974, now patent No. 3,948,961, the disclosure of which is hereby incorporated by reference. Cyclopropylmethyl alcohol is available commercially.

The acids can be prepared by treating an alcohol of the formula

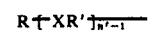

OH with an organolithium compound to form the salt

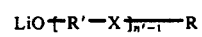

treating this salt with hexamethylphosphoric triamide and tetrahydrofuran followed by the sodium salt of 2-iodoacetic acid or 2-iodopropionic acid and then hydrolysing to yield the acid. Suitable methods are described also in S. African Pat. Nos. 64/6736–8.

Many of the alcohols

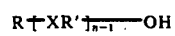

are commercially available or can be prepared by conventional methods well known in the art including the methods disclosed in copending Ser. No. 504,224, now U.S. Pat. No. 3,957,849, filed Sept. 9, 1974, the disclosure of which is hereby incorporated by reference.

The term "alkyl", as used herein, refers to a straight or branched chain saturated aliphatic hydrocarbon group of one to eighteen carbon atoms, e.g. methyl, ethyl, propyl, octyl, 2-methyloctyl, undecyl, pentadecyl, and the like. The term "lower alkyl" refers to an alkyl group of one to six carbon atoms.

The term "alkenyl", as used herein, refers to a straight or branched chain hydrocarbon group of two to eighteen carbon atoms having one or two sites of olefinic unsaturation.

The term "alkynyl", as used herein, refers to a straight or branched chain hydrocarbon group of two to eighteen carbon atoms having one or two sites of acetylenic unsaturation.

The term "ethylene", as used herein, refers to the group, —CH$_2$—CH$_2$— or the group,

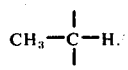

The esters of the present invention can be used alone or in an inert carrier substance for the control of mites (Acarina) or can be used in mixture with pesticides, fungicides and/or juvenile hormone analogs known in the art in order to obtain a broader spectrum of activity. Suitable insecticides include Baygon, Captan, Sevin, Ciodrin, Systox, Diazinon, Vapona, Galecron, Cygon, Dimethrin, Dursban, Malathion, Resmethrin and Parathion. Typical juvenile hormone analogs which can be used in mixture with the compound of the present invention are described in U.S. Pat. Nos. 3,752,843 and 3,904,662.

The esters of the present invention are useful for the control of mites and ticks which are ectoparasitic on domestic animals including birds. The compounds can be applied in either solution or in powder (dust) form in a conventional manner.

The following examples are provided to illustrate the synthesis of the esters of the present invention and the practice of the present invention. Temperature is in degrees Centigrade. All boiling points were measured by short path distillation.

EXAMPLE 1

To a mixture of 9.6 g. 1-tridecanol and 100 ml. tetrahydrofuran at 0° is added 33.5 ml. of 1.43 M n-butyllithium in hexane solution over a 5 minute period. The ice-bath is then removed and the mixture is stirred at room temperature. The solvent is removed by rotary evaporation, yielding a colorless viscous liquid. To this residue is added 100 ml. tetrahydrofuran and 50 ml. hexamethylphosphoric triamide followed by 20 g. sodium 2-iodoacetate. The mixture is stirred overnight at room temperature and then boiled for 8.5 hours. After cooling to room temperature, 150 ml. methanol, 75 ml. water and 3.8 g. sodium hydroxide pellets are added. After the sodium hydroxide pellets are dissolved, the mixture is boiled for 12 hours and then maintained at room temperature for 15 days. Volatile material is removed by rotary evaporation (65° at 80 mm.) and to the residue is added 400 ml. of a 2:1 mixture of ether and pentane and 200 ml. water. The lowest phase of the resultant triphasic mixture is removed and discarded. The remaining biphasic mixture is washed, with water (2 × 100 ml.). Ethyl acetate (200 ml.), water (100 ml.) and aqueous 3N sulfuric acid (120 ml.) are then added. After vigorous shaking, the lower phase (now reduced in volume) is removed. The remaining upper phase is washed with aqueous saturated sodium chloride (2 × 50 ml.), is dried over calcium sulfate and the solvent is removed by rotary evaporation to yield 6.53 g. 3-oxahexadecanoic acid as a pale yellow solid.

Similarly, 2-methyl-3-oxahexadecanoic acid is prepared from tridecanol and sodium 2-iodopropionate using the procedure of Example 1.

Table 1 summarizes the acids prepared by the method of Example 1 by reacting each of sodium 2-iodoacetate and sodium 2-iodopropionate with each of the following compounds: 1-tridecanethiol, 1-dodecanol, 1-tetradecanol, 1-pentadecanol, 1-nonanethiol, 1-pentanethiol, 2-hexyn-1-ol, 10,12-tetradecadien-1-ol, 9-hexadecen-1-ol, and ethanol.

| I |
|---|
| 3-thiahexadecanoic acid |
| 2-methyl-3-thiahexadecanoic acid |
| 3-oxapentadecanoic acid |
| 2-methyl-3-oxapentadecanoic acid |
| 3-oxaheptadecanoic acid |
| 2-methyl-3-oxaheptadecanoic acid |
| 3-oxaoctadecanoic acid |
| 2-methyl-3-oxaoctadecanoic acid |
| 3-thiadodecanoic acid |
| 2-methyl-3-thiadodecanoic acid |
| 3-thiaoctanoic acid |
| 2-methyl-3-thiaoctanoic acid |
| 3-oxa-5-nonynoic acid |
| 2-methyl-3-oxa-5-nonynoic acid |
| 3-oxa-13,15-heptadecadienoic acid |
| 2-methyl-3-oxa-13,15-heptadecadienoic acid |
| 3-oxa-12-nonadecenoic acid |
| 2-methyl-3-oxa-12-nonadecenoic acid |
| 3-oxapentanoic acid |
| 2-methyl-3-oxapentanoic acid |

EXAMPLE 2

To a mixture of 2.58 g. 3-oxahexadecanoic acid, 40 ml. anhydrous ether, and 1.1 ml. thionyl chloride at room temperature is added 0.2 ml. of dimethylformamide. The mixture is stirred overnight, the top phase of the resultant biphasic mixture is separated and the volatile material removed from it by rotary evaporation. To the residue is added 60 ml. anhydrous ether, 1.1 g. cyclopropylmethanol and, at 0°, 1.6 ml. pyridine. The ice bath is removed and the mixture is stirred at room temperature for 4 days. Ether (50 ml.), pentane (50 ml.) and water (100 ml.) are added and the mixture is acidified with aqueous 3N sulfuric acid. The organic layer is separated and washed, in turn, with aqueous 15% potassium carbonate (1 × 50 ml.), water (2 × 50 ml.), aqueous saturated copper sulfate (1 × 50 ml.), water (1 × 50 ml.), and aqueous saturated sodium chloride (1 × 50 ml.) and then is dried over calcium sulfate. The solvent is removed to yield 2.13 g. of product which is purified by distillation to yield cyclopropylmethyl 3-oxahexadecanoate b.p. 111°–123° at 0.05 mm.

Following the procedure of Example 2, the acids of Column I are reacted with cyclopropylmethanol, 3-cyclopropylpropanol, 5-cyclopropylpentanol, 7-cyclopropylheptanol, 9-cyclopropylnonanol, 11-cyclopropylundecanol, and 13-cyclopropyltridecanol. Representative compounds of this invention that are prepared in the above manner are listed in Table II.

| II |
|---|
| cyclopropylmethyl 3-thiahexadecanoate |
| 3-cyclopropylpropyl 2-methyl-3-thiahexadecanoate |
| cyclopropylmethyl 3-oxapentadecanoate |
| 3-cyclopropylpropyl 2-methyl-3-oxapentadecanoate |
| cyclopropylmethyl 3-oxaheptadecanoate |
| cyclopropylmethyl 2-methyl-3-oxaheptadecanoate |
| cyclopropylmethyl 3-oxaoctadecanoate |
| cyclopropylmethyl 2-methyl-3-oxaoctadecanoate |
| 3-cyclopropylpropyl 3-thiadodecanoate |
| 5-cyclopropylpentyl 2-methyl-3-thiadodecanoate |
| 9-cyclopropylnonyl 3-thiaoctanoate |
| 7-cyclopropylheptyl 2-methyl-3-thiaoctanoate |
| 9-cyclopropylnonyl 3-oxa-5-thianonynoate |
| 7-cyclopropylheptyl 2-methyl-3-oxa-5-thinonynoate |
| cyclopropylmethyl 3-oxa-13,15-heptadecadienoate |
| cyclopropylmethyl 2-methyl-3-oxa-13,15-heptadecadienoate |
| cyclopropylmethyl 3-oxa-12-nonadecanoate |
| cyclopropylmethyl 2-methyl-3-oxa-12-nonadecenoate |

-continued

| II |
|---|
| 11-cyclopropylundecyl 3-oxapentanoate |
| 13-cyclopropyltridecyl 2-methyl-3-oxapentanoate |

A wettable powder suitable for field application after dilution can be formulated by blending and then air-milling a mixture of 20 to 30% of an ester of this invention, 60 to 70% of a solid carrier such as Attaclay X-250, 1 to 3% of an anionic surfactant, such as Igepon T-77, and 3 to 5% of a dispersing agent such as Marasperse N-22.

A typical formulation is as follows:

| Active ingredient[1] | 25.0% |
|---|---|
| Synthetic calcium silicate | 40.0% |
| Attapulgite Clay | 29.0% |
| Sodium lignosulfonate | 4.0% |
| Sodium N-methyl N-oleoyl taurate | 2.0% |

[1]The active ingredient is selected from one or more of the following:
   cyclopropylmethyl 3-oxahexadecanoate
   cyclopropylmethyl 3-thiahexadecanoate
   3-cyclopropylpropyl 3-oxatetradecanoate The mite control agents of the present invention can be used alone in an inert agriculturally acceptable carrier substance for the control of mites (Acarina) or can be used in mixture with insecticides and/or juvenile hormone analogs known in the art to provide a broader spectrum of activity on more developmental stages of the mites or on other pestiferous insect species.

The effectiveness of the compounds of the present invention is demonstrated below.

Adults of Tetranychus urticae are allowed to oviposit for 24 hours on castor bean leaf discs (diameter 1 cm.) on moist cottonwool.

After 24 hours, the adults are removed and the leaf discs are then dipped in acetone solutions of the compound being tested.

After submersion for one second, the solvent on the leaf discs is allowed to dry and the leaf discs are then glued to a plastic petri dish to prevent crumpling.

Six days later (when all the eggs on untreated discs have emerged), the number of unhatched eggs is calculated as a percentage of the total number originally present and corrected for any spontaneous non-emergence observed in control discs treated only with solvent (Abbott correction).

At a 0.1 percent concentration of cyclopropylmethyl 3-oxahexadecanoate in acetone, the mortality of the eggs is 96%.

What is claimed is:

1. Compounds selected from those of formula I

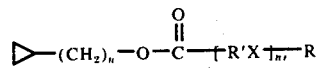

wherein,
R is alkyl of one to eighteen carbon atoms, alkenyl of two to eighteen carbon atoms, or alkynyl of two to eighteen carbon atoms;
R' is methylene or ethylene;
X is oxygen or sulfur;
$n$ is an odd integer between one and thirteen; and
$n'$ is one, two, or three;
with the proviso that each compound contains at least twelve carbon atoms in the molecule.

2. Compounds according to claim 1 wherein $n$ is an odd integer between one and seven and $n'$ is one or two.

3. Compounds according to claim 2 wherein R' is methylene.

4. Compounds according to claim 3 wherein R is alkyl of ten to fifteen carbon atoms, alkenyl of ten to fifteen carbon atoms, or alkynyl of ten to fifteen carbon atoms.

5. Compounds according to claim 4 wherein $n'$ is one and R is alkyl of ten to fifteen carbon atoms.

6. The compound, cyclopropylmethyl 3-thiahexadecanoate, according to claim 5.

7. Compounds according to claim 5 wherein X is oxygen.

8. The compound cyclopropylmethyl 3-oxahexadecanoate, according to claim 7.

* * * * *